(12) United States Patent
Wahlstrand et al.

(10) Patent No.: US 8,934,973 B2
(45) Date of Patent: Jan. 13, 2015

(54) HUB FOR IMPLANTABLE MEDICAL LEADS (75) Inventors: Carl D. Wahlstrand, North Oaks, MN (US); Dale F. Seeley, Spring Park, MN (US); Gabriela C. Molnar, Fridley, MN (US); Lisa M. Johanek, White Bear Lake, MN (US)

(73) Assignee: Medtronic, Inc., Minneapolis, MN (US)

( * ) Notice: Subject to any disclaimer, the term of this patent is extended or adjusted under 35 U.S.C. 154(b) by 206 days.

(21) Appl. No.: 13/376,141

(22) PCT Filed: Jun. 21, 2010

(86) PCT No.: PCT/US2010/039299
§ 371 (c)(1),
(2), (4) Date: Dec. 2, 2011

(87) PCT Pub. No.: WO2010/148379
PCT Pub. Date: Dec. 23, 2010

(65) Prior Publication Data
US 2012/0083867 A1    Apr. 5, 2012

Related U.S. Application Data (60) Provisional application No. 61/218,452, filed on Jun. 19, 2009.

(51) Int. Cl.
*A61N 1/05* (2006.01)
*H04L 12/18* (2006.01)
*H04L 12/58* (2006.01)
*H04W 72/00* (2009.01)
*H04W 72/12* (2009.01)

(52) U.S. Cl.
CPC .......... *H04L 12/189* (2013.01); *H04L 12/5895* (2013.01); *H04L 51/38* (2013.01); *H04W 72/005* (2013.01); *H04W 72/1273* (2013.01); *H04W 72/1289* (2013.01)
USPC ............................................. 607/36; 607/116

(58) Field of Classification Search
USPC ....................................................... 607/36, 116
See application file for complete search history.

(56) References Cited

U.S. PATENT DOCUMENTS 5,374,279 A * 12/1994 Duffin et al. ...................... 607/5
5,383,913 A *  1/1995 Schiff ............................. 607/38
5,690,611 A    11/1997 Swartz et al.
7,242,987 B2   7/2007 Holleman et al.
(Continued)

OTHER PUBLICATIONS

PCT/US10/039299: Search Report and Written Opinion dated Sep. 6, 2010.

(Continued)

*Primary Examiner* — Alyssa M Alter
(74) *Attorney, Agent, or Firm* — Mueting, Raasch & Gebhardt, P.A.

(57) ABSTRACT

A hub (200) includes a first lead receptacle having a plurality of contacts (280) for electrically coupling a lead to an implantable electrical device. The hub further contains a second lead receptacle having a plurality of contacts for electrically coupling a lead to the implantable electrical device. At least one of the plurality of contacts of the first receptacle is a contact of the second receptacle. Such a configuration may allow for the overall size of the hub to be reduced relative to a hub where each discrete contact of the hub corresponds to a discrete contact or electrical channel of the implantable electrical device.

13 Claims, 11 Drawing Sheets

(56) References Cited

U.S. PATENT DOCUMENTS

| | | |
|---|---|---|
| 7,515,964 B1 | 4/2009 | Alexander et al. |
| 7,933,652 B2 | 4/2011 | Phillips et al. |
| 2007/0239155 A1 | 10/2007 | Ibrahim et al. |
| 2008/0269716 A1 | 10/2008 | Bonde et al. |

OTHER PUBLICATIONS

PCT/US10/039300: Search Report and Written Opinion dated Oct. 26, 2010.

\* cited by examiner

HUB FOR IMPLANTABLE MEDICAL LEADS

RELATED APPLICATION

This application is a U.S. National Stage filing under 35 U.S.C. 371 of copending PCT Application Serial No. PCT/US2010/039299, filed Jun. 21, 2010, which claims the benefit of priority to U.S. provisional patent application No. 61/218,452, filed Jun. 19, 2009, both of which applications are incorporated herein by reference to the extent that they do not conflict with the present disclosure.

FIELD

This disclosure relates to implantable medical systems employing implantable medical leads; and more particularly, to hubs for operably coupling implantable medical leads to active implantable medical devices such as implantable medical signal generators.

BACKGROUND

Many implantable medical devices, such as neurostimulators, pacemakers and defibrillators, transmit electrical signals to provide therapy to a patient. Implantable medical leads deliver signals generated from such devices to tissue of the patient via one or more electrodes of the lead. Often the electrodes of the leads are located at a considerable distance from the implant location of the electrical signal generator device. If multiple leads are required or desired, separate subcutaneous paths may need to be tunneled for each lead, resulting in time consuming surgical procedures and potential patient discomfort.

In some situations a lead extension is employed to couple the lead to the signal generator. The lead extension may allow for connection of the lead in closer proximity to the tissue to which the generated electrical signal is applied, reducing the extent of tunneling required for the lead. However, the extension still needs to be tunneled through the patient.

When it is desired to implant two leads in the same general tissue location, a bifurcated lead extension with a single proximal leg may be employed. In such cases, one tunneling path may be made from the implant location of the electrical signal generation to a location close to the target tissue for the lead extension. The two leads may then be coupled to the extension at this location and may then traverse relatively short distances in the patient.

However, if more than two leads are desired, a single bifurcated extension is not sufficient and more than one extended subcutaneous tunneling procedure may be required. Further, bifurcated lead extensions tend to be of limited flexibility in terms of functionality. For example, if a proximal end of a bifurcated lead extension has eight discrete electrical contacts for making eight discrete electrical connections with an electrical signal generator, the bifurcated distal end will have two separate lead receptacles, each having four internal contacts for making electrical connections with four discrete contacts of a lead.

BRIEF SUMMARY

The present disclosure describes, among other things, a hub for electrically coupling a lead with an active implantable electrical device. The hub may be used to operably couple two or more leads to the electrical device. The hub may be implanted in proximity to a tissue site to which a lead is implanted, reducing the number of extended tunneling procedures that need to be done. In various embodiments, the hub may couple leads having differing numbers of contacts. In some embodiments, the hub is configured to reduce overall size while still providing functional flexibility.

For example, a hub may include a first lead receptacle having a plurality of contacts for electrically coupling a lead to an implantable electrical device. The hub may further contain a second lead receptacle having a plurality of contacts for electrically coupling a lead to the implantable electrical device. At least one of the plurality of contacts of the first receptacle may be a contact of the second receptacle. Such a configuration may allow for the overall size of the hub to be reduced relative to a hub where each discrete contact of the hub corresponds to a discrete contact or electrical channel of the implantable electrical device.

By way of further example, a system may include an implantable electrical medical device and a hub. The implantable electrical medical device is capable of generating electrical signals on a plurality of discrete channels. The hub is configured to electrically couple one or more leads to the electrical device. The hub has a plurality of internal contacts electrically coupled to the electrical device, wherein each of plurality of internal contacts is electrically coupled to the device via one of the discrete channels. The number of internal contacts of the hub is greater than the number of discrete channels of the electrical device.

The drawings are not necessarily to scale. Like numbers used in the figures refer to like components, steps and the like. However, it will be understood that the use of a number to refer to a component in a given figure is not intended to limit the component in another figure labeled with the same number. In addition, the use of different numbers to refer to components is not intended to indicate that the different numbered components cannot be the same or similar.

DETAILED DESCRIPTION

In the following detailed description, reference is made to the accompanying drawings that form a part hereof, and in which are shown by way of illustration several specific embodiments of devices, systems and methods. It is to be understood that other embodiments are contemplated and may be made without departing from the scope or spirit of the devices, systems and methods described herein. The following detailed description, therefore, is not to be taken in a limiting sense.

All scientific and technical terms used herein have meanings commonly used in the art unless otherwise specified. The definitions provided herein are to facilitate understanding of certain terms used frequently herein and are not meant to limit the scope of the present disclosure.

As used in this specification and the appended claims, the singular forms "a", "an", and "the" encompass embodiments having plural referents, unless the content clearly dictates otherwise.

As used in this specification and the appended claims, the term "or" is generally employed in its sense including "and/or" unless the content clearly dictates otherwise.

The present disclosure describes, among other things, a hub for electrically coupling a lead with an active implantable electrical device. The hub may be used to operably couple two or more leads to the electrical device. The hub may be implanted in proximity to a tissue site to which a lead is implanted, reducing the number of extended tunneling procedures that need to be done. In various embodiments, the hub may couple leads having differing numbers of contacts. In some embodiments, the hub is configured to reduce overall size while still providing functional flexibility.

The teachings presented herein are applicable to any implantable medical device system employing lead for delivering electrical signals to a tissue of a patient. For example, the system may include a neurostimulator, such as a peripheral nerve stimulator, a spinal cord stimulator, or a deep brain stimulator; a cardiac pacemaker or defibrillator; a gastric stimulator; or the like. It will be understood that the systems and devices described herein may be readily applied to systems employing leads for purposes of sensing, monitoring, recording, or the like.

Figure 1:
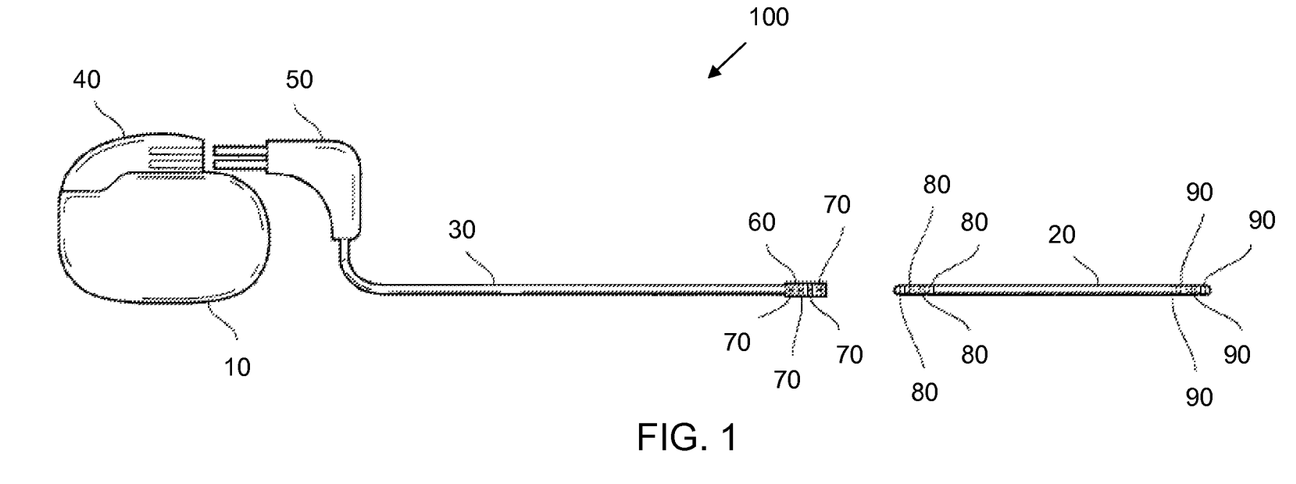
FIG. 1 is a schematic side view of a generic implantable electrical system.

Referring to FIG. 1, a schematic side view of a system 100 employing a generic lead extension 30 is shown. The system 100 also includes an implantable electrical signal generator 10 and a lead 20. Implantable electrical signal generator 10 includes a connector header 40 configured to receive plug 50 at proximal end of lead extension 30 or other adaptor to couple lead 20 to electrical signal generator 10. The distal end portion of lead extension 30 includes a connector 60 configured to receive proximal end portion of lead 20. Connector 60 includes internal electrical contacts 70 configured to electrically couple extension 30 to lead 20 via electrical contacts 80 disposed on the proximal end portion of lead 20. Electrodes 90 are disposed on distal end portion of lead 20 and are electrically coupled to electrical contacts 80, typically through conductors (not shown). In general, a lead 20 may include any number of electrodes 90, e.g. one, two, three, four, five, six, seven, eight, or sixteen. Typically, each electrode 90 is electrically coupled to a discrete electrical contact 80.

Figure 2:
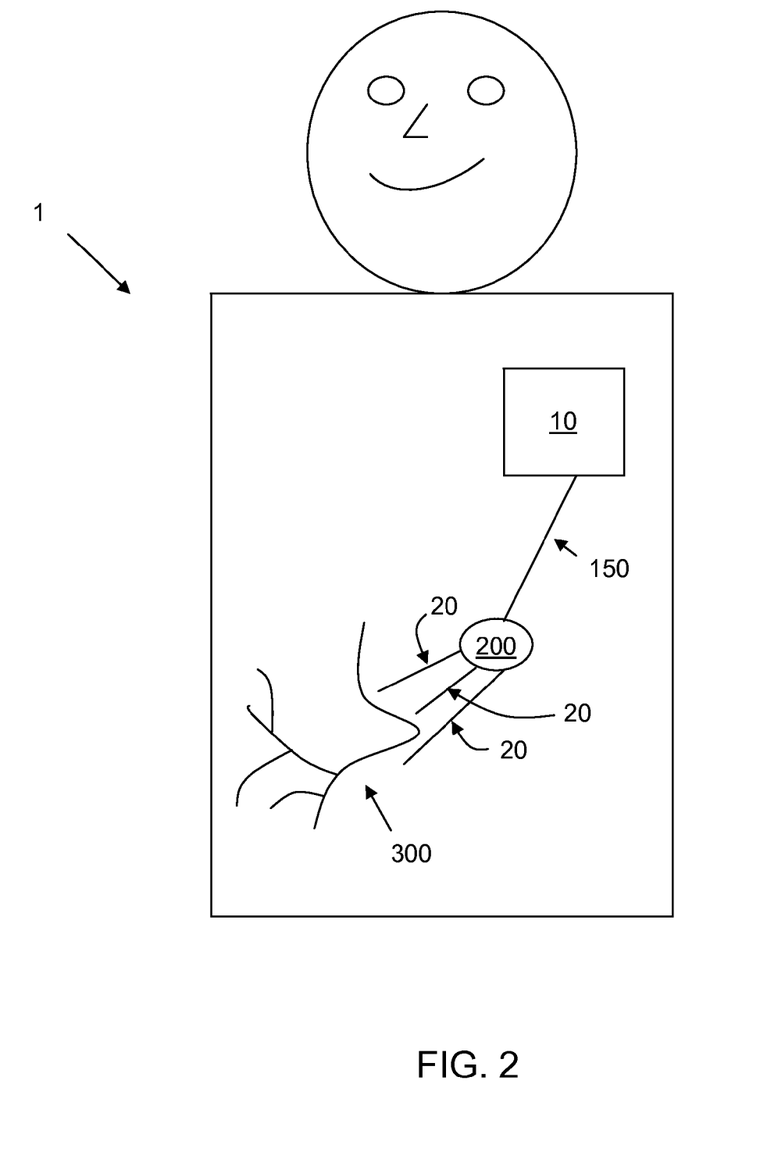
FIG. 2 is a schematic drawing of showing a generic implantable electrical system and a generic target nerve in a patient.

A hub as described herein, in many respects, may be similar to a lead extension as described above with regard to FIG. 1. Referring now to FIG. 2, a hub 200 is electrically coupled to an implantable electrical device 10, e.g. via a cable 150 carrying one or more conductors or wires (not shown). The cable 150 may include electrical contacts for electrically connecting to internal contacts of the device 10 when the cable 150 is inserted into the device 10. As shown in FIG. 2, one or more leads 20 may be operably coupled to the hub 200, which in turn operably couples the leads 20 to the device 10. The leads 20 depicted in FIG. 2 are positioned to apply electrical signals to a nerve 300, such as a peripheral nerve, of a patient 1. However, it will be understood that the leads 20 may be positioned or configured to apply or sense signals from any suitable tissue of the patient 1. For example, in peripheral nerve stimulation for the treatment of pain, multiple leads may be used to target multiple pain areas or multiple nerve targets or multiple tissue targets (such as a scar or subcutaneous tissue areas). While not shown, it will be understood that more than one hub 200 may be operably coupled to one electrical device 10.

Figure 3:
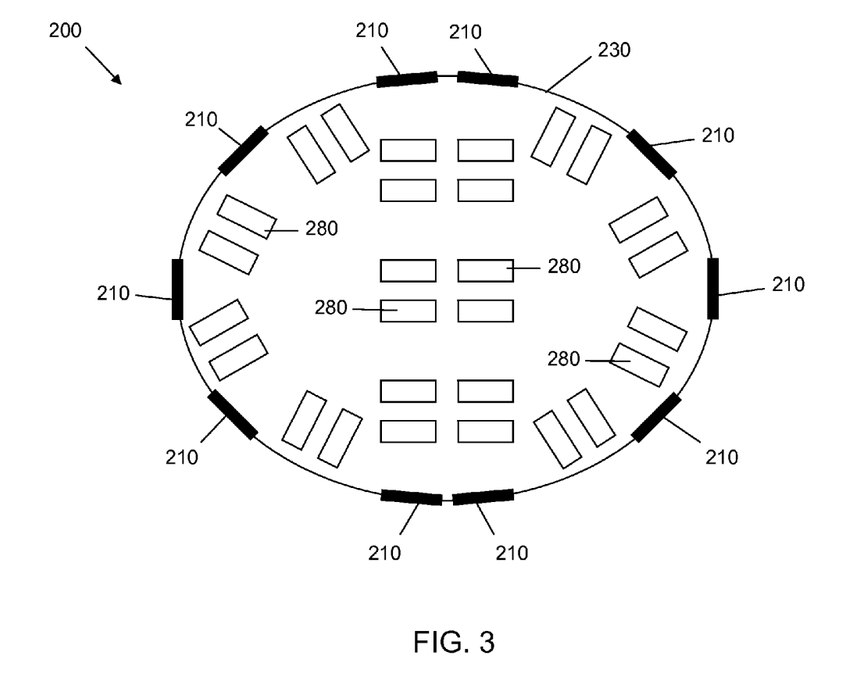
FIG. 3 is a schematic drawing of a hub showing lead entry ports and internal contacts.
Figure 4:
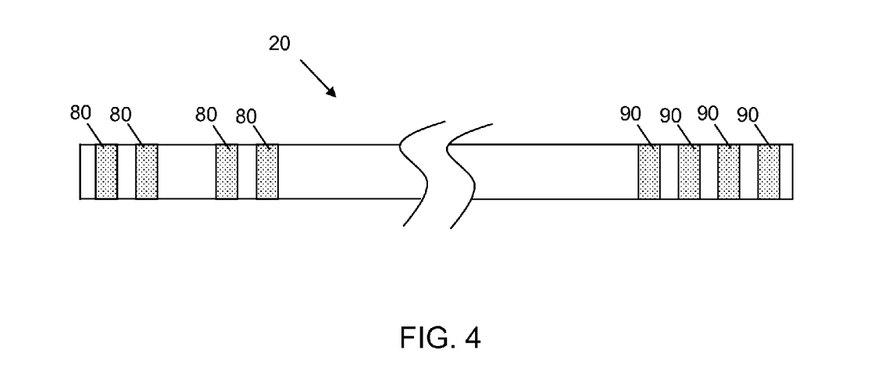
FIG. 4 is a schematic side view of a lead having contacts configured to electrically couple with internal contacts of a hub, such as a hub depicted in FIG. 3.

Referring now to FIG. 3, a schematic drawing of some components of a hub 200 is shown. In the depicted hub 200, only an outline of the hub housing 230, lead entry ports 210 and internal contacts 280 are shown. It will be understood that hub 200 may include additional components, such as conductors electrically coupled to the contacts 280 and a cable for connection to an electrical device, even though such components are not shown. FIG. 4 depicts a lead 20 having contacts 80 spaced apart in a manner suitable for electrically coupling to contacts 280 of a hub 200 as depicted in FIG. 3. Of course the contacts 280 of the hub 200 and the contacts 80 of the lead 20 may be spaced in any suitable manner.

Figure 5:
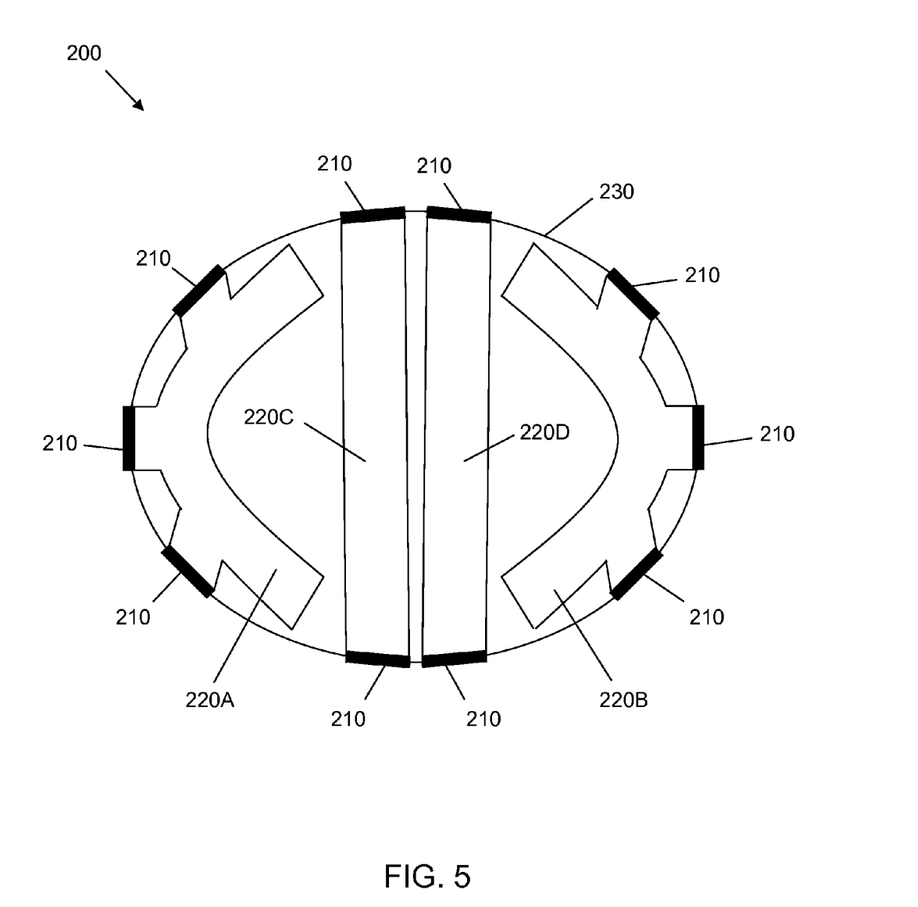
FIG. 5 is a schematic drawing of a hub showing tracks of bores.

Referring now to FIG. 5, tracks or bores 220A, 220B, 220C, 220D of the hub 200 are shown. The bores 220A, 220B, 220C, 220D are in communication with the lead entry ports 210 of the hub 200. The bores 220A, 220B, 220C, 220D may be rectilinear or non-rectilinear.

Figure 6:
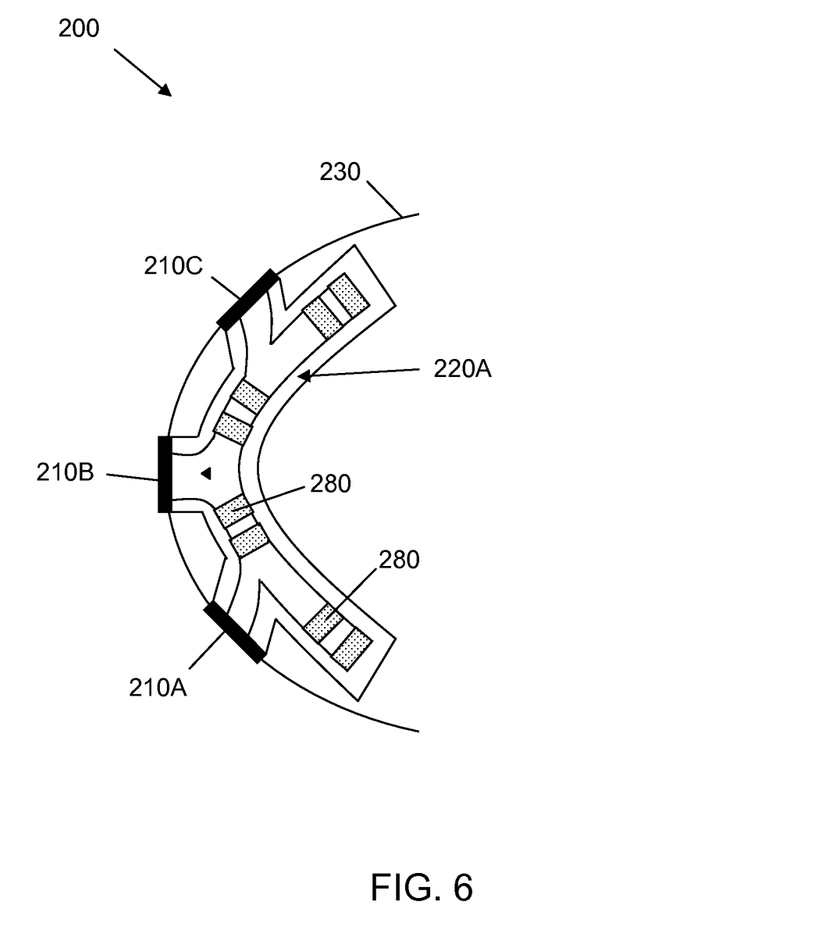
FIG. 6 is a schematic drawing of a portion of hub showing a track of a bore and internal contacts disposed in the bore.

With reference to FIG. 6, a schematic sectional view of a portion of the hub 200 through one of the bores 220A is shown. As shown in more detail, openings of the lead entry ports 210A, 210B, 210C are in communication with the bore 220A. Contacts 280 are disposed in the bore 280 and are configured to electrically couple to contacts of a lead inserted into an entry port 210A, 210B, 210C. The bore and each entry port 210A, 210B, 210C forms a lead receptacle into which a lead may be inserted such that electrical contact can be made. Alternatively, a lead receptacle, such as those employed in implantable electrical signal generators or lead extensions, may be housed in the bore. In either case, the bore will be considered to form a lead receptacle for the purposes of the present disclosure.

Figure 7:
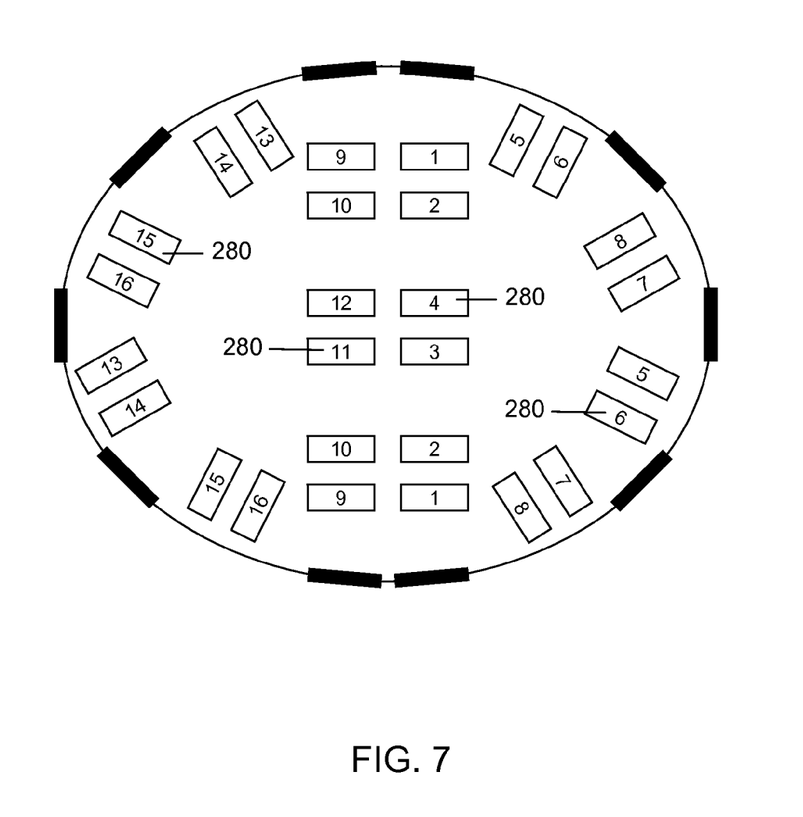
FIG. 7 is a schematic drawing of a hub showing lead entry ports and internal contacts.

Referring now to FIG. 7, which is an embodiment of the hub 200 depicted in FIG. 3, internal contacts 280 of the hub are numbered according to which channel of a 16-channel electrical signal generator the contacts 280 are configured to couple. As can be seen, the hub may have redundant contacts 280 capable of coupling to a given channel of the signal generator. Such a configuration allows for a great deal of flexibility regarding how leads may be operably coupled with the hub.

Figure 8:
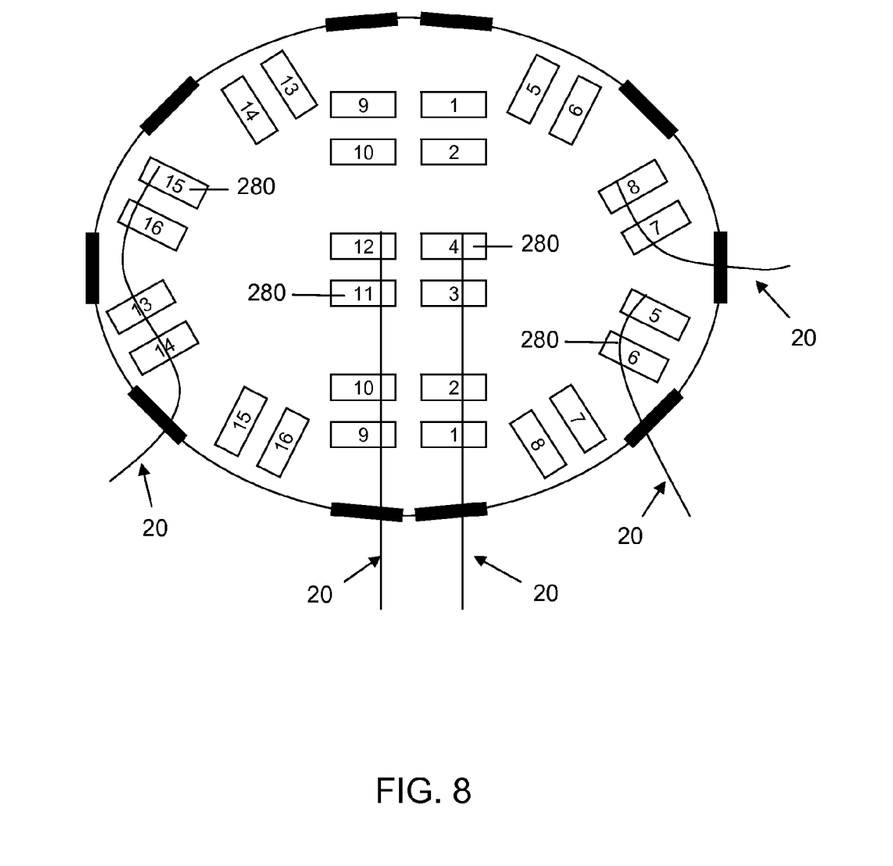
FIG. 8 is a schematic drawing of a hub showing lead entry ports and internal contacts and leads inserted into the hub.
Figure 9:
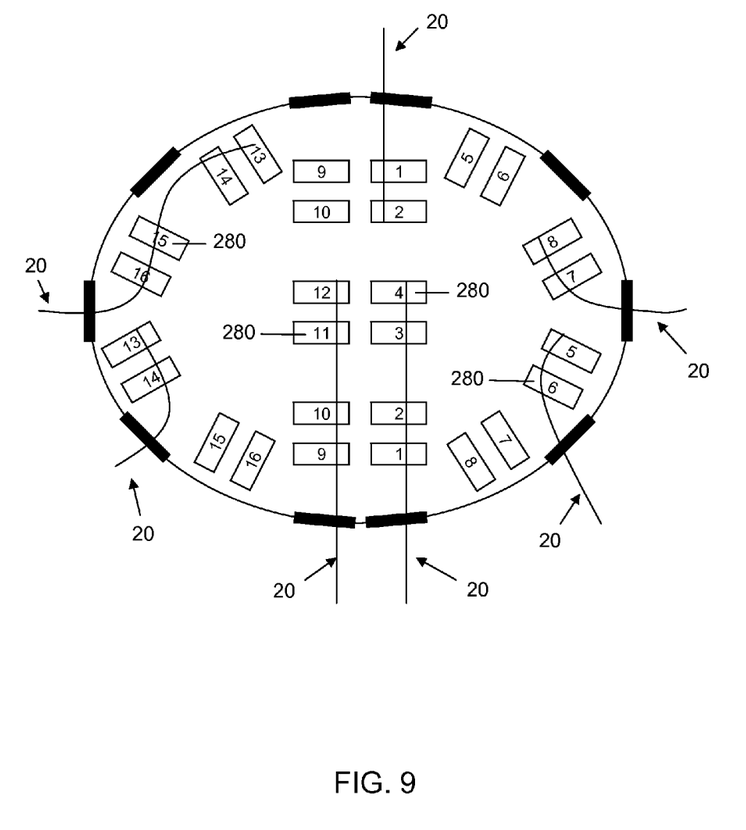
FIG. 9 is a schematic drawing of a hub showing lead entry ports and internal contacts and leads inserted into the hub.

For example and with reference to FIGS. 8-9, some possible configurations of leads 20 employed in connection with a hub are shown. In FIG. 8, each lead 20 is coupled to a contact 280 that is coupled or couplable to a discrete channel of an electrical device, such as a signal generator. In FIG. 8, five leads 20 are operably coupled with the hub. Three of the leads are coupled to four contacts 280 (corresponding to channels 1, 2, 3, and 4; 9, 10, 11, and 12; and 13, 14, 15, and 16 of the signal generator), and two of the leads 20 are coupled to two contacts 280 (corresponding to channels 5 and 6; and 7 and 8 of the signal generator). In FIG. 9, seven leads 20 are operably coupled with the hub. Note that some of the leads 20 are coupled to redundant contacts 280 (i.e., contacts corresponding to the same channel of the signal generator). For example, one lead 20 is coupled to contacts 280 corresponding to channels 1, 2, 3 and 4 of the signal generator and another lead 20 is coupled to contacts 280 corresponding to channels 1 and 2 of the signal generator.

In the embodiments, depicted in FIGS. 7-9, each of the contacts 280 of the hub corresponding to a given channel of the signal generator may receive a signal when a channel is activated. Alternatively, a switch or sensor may be employed to determine which contacts are coupled to leads, and only those coupled contacts may be activated when a channel sends a signal. In one example, the sensor could be electrical as when using an electrical impedance test in unipolar or bipolar fashion. When using this test, contacts 280 of the hub that are connected to a lead 20 will detect an impedance within a certain range suggestive of good electrical contact from the signal generator to the electrodes on the appropriate lead(s) 20, for example between 100 and 4000 ohms. If a lead 20 is not connected to a contact 280 at the hub, the impedance test will detect an open circuit, i.e. a very high impedance value, and no stimulation would be delivered to those contacts 280. In another example, the sensor could be mechanical, as in activation of a switch at the contact 280 that allows current flow through that specific contact 280 only when a lead 20 touching the contact 280 on the hub. In one example, a contact 280 in the hub may consist of two surfaces that slightly expand when a lead 20 is placed within the contact. The expansion of these surfaces may create an electrical connection that will indicate to the device or signal generator that there is a lead 20 within the contact 280. In some embodiments, a switch or sensor may be activated when a lead 20 is inserted into an entry port. In some embodiments, a sensor may be employed with regard to each contact 280 of the hub.

In some embodiments, a multiplexer (not shown) and demultiplexer (not shown) may be employed to limit the number of conductors that run between the electrical signal generator and the hub. For example, a multiplexer may be employed in the signal generator and a demultiplexer may be employed in the hub. In addition or alternatively, a demultiplexer may be employed in the hub to allow for creation of subchannels such that different contacts 280 corresponding to the same channel may be activated at different times to effectively increase the number of channels. The different contacts 280 may be connected to different electrodes on the same lead 20 or two one or more contacts 280 on multiple other leads 280.

It will be understood that the configuration of internal hub contacts 280 presented in FIGS. 7-9 are merely an illustration of the configurations that may be employed. It will also be understood that a hub as described herein may be coupled to a signal generator or other electrical device having any number of channels.

Figure 10A:
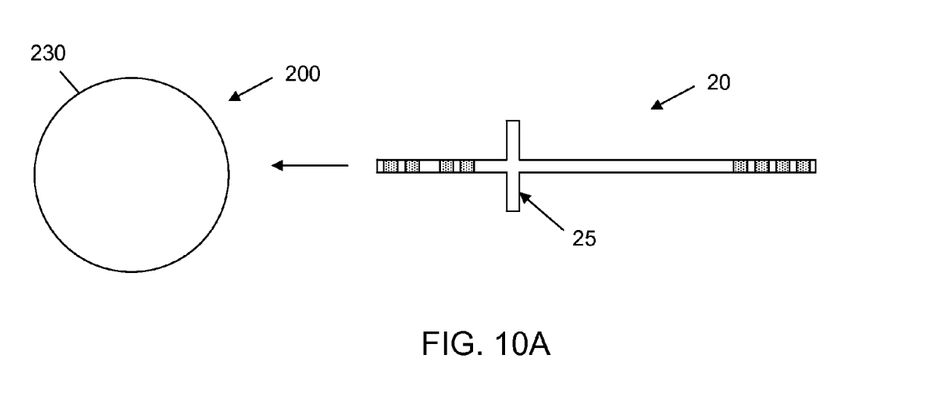
FIGS. 10A-B are schematic top views of a lead and a hub.
Figure 10B:
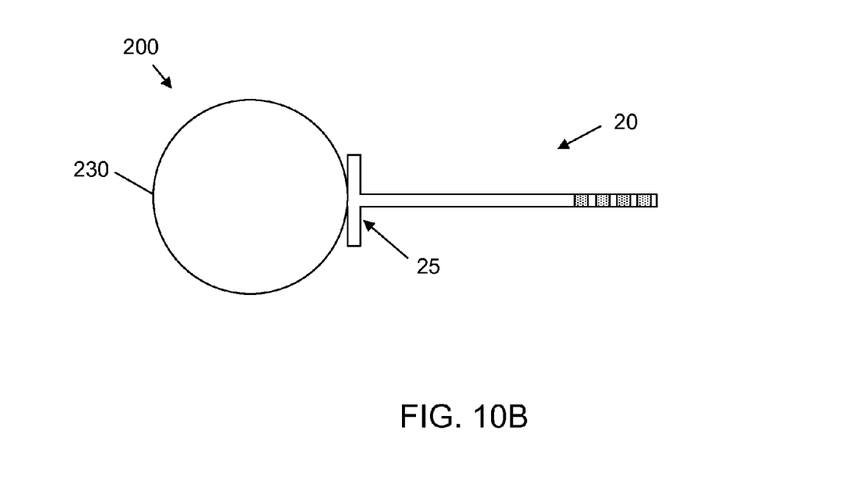

Referring now to FIGS. 10A-B, a lead 20 prior to insertion into a hub 200 (FIG. 10A) and after insertion into the hub 200 (FIG. 10B) is shown. The lead 20 includes a stop mechanism 25 configured to engage the housing 230 of the hub 200 to ensure that the contacts of the lead 20 properly align with internal contact of the hub 200. The stop mechanism 25 may be a bump or protrusion, bar, plate, or the like. The position of the stop mechanism 25 relative to the distal end of the lead 20 may vary depending on the number of contacts the lead has or are configured to engage internal contacts of the hub 200 (e.g., two or four contacts as depicted in FIGS. 8-9). The stop mechanism 25 may be moveable, e.g. slidable, along the length of the lead 20 or may be permanently fixed to the lead body. Alternatively or in addition, the lead 20 may include a visible marker (not shown) that indicated when the lead is fully and properly inserted into the hub. For example, a marker band may be aligned with the exterior of the hub 200 at a port to indicate that the lead 20 is properly inserted and the contacts of the lead are aligned with the contacts of the hub. A lead 20 may include more than one such marker to allow for insertion into the hub 200 by an amount that couples a desired number of contacts of the lead with a desired number of contacts of the hub. If the lead includes a moveable stop mechanism 25, the markers may be used to indicate proper positioning of the stop mechanism for fixation relative to the lead.

As shown in the embodiments depicted in FIGS. 8-9, it may be desirable for the distal regions of the leads to be sufficiently flexible to follow the path of the contacts of the hub (e.g., defined by a bore as depicted in FIGS. 5-6), yet sufficiently rigid to be fully inserted into the hub. Thus, it may be desirable for the angles of the path of the bores in the hub to not be too sharp.

The leads 20 may be fixed relative to the hub 200 through any suitable mechanism. For example, the hub 200 may include one or more set screws (not shown) for securing the lead relative to the hub when the lead is inserted into a lead receptacle or bore of the hub. Such set screws are well known for lead extensions and implantable electrical signal generators and may be readily adopted for use with the hubs described herein. Alternatively or in addition, any of a variety of screw-less securing mechanisms that have been developed for used with lead extensions, implantable electrical signal generators, or the like may be readily adopted for use with the hubs described herein.

Figure 11:
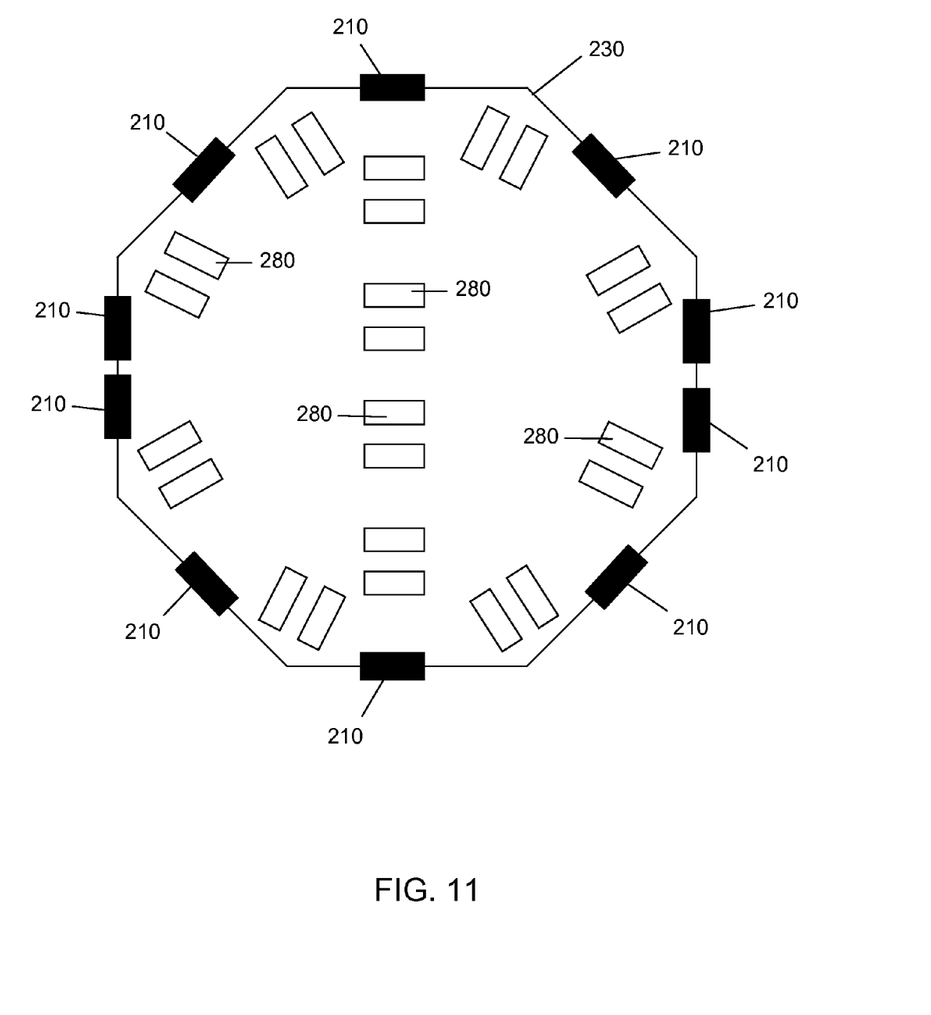
FIG. 11 is a schematic drawing of a hub showing lead entry ports and internal contacts.
Figure 12:
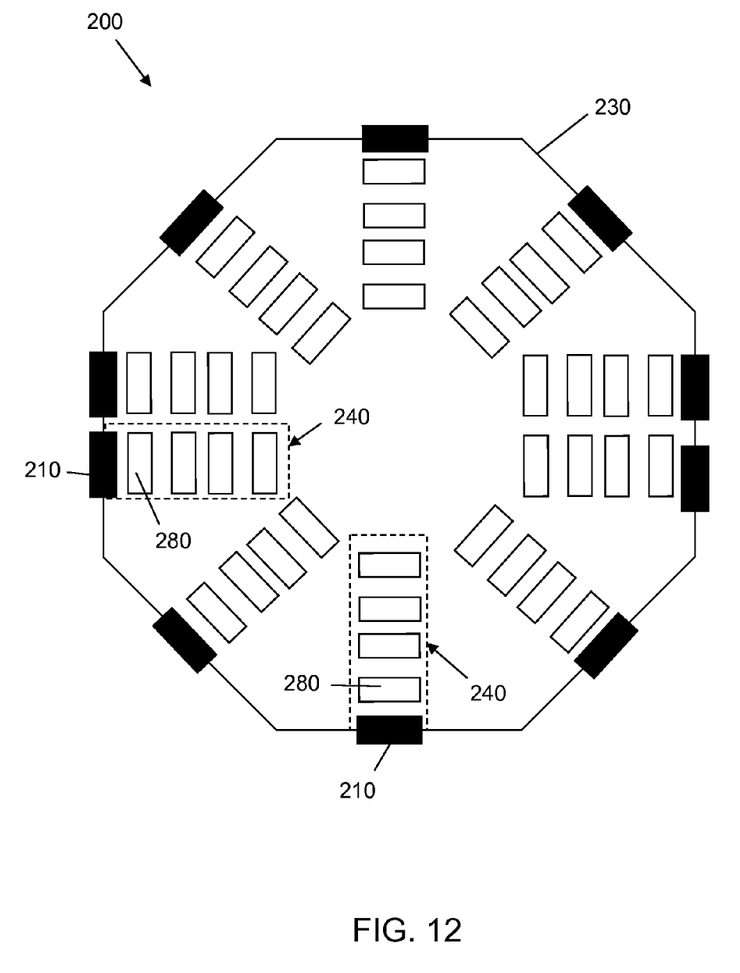
FIG. 12 is a schematic drawing of a hub showing lead entry ports and internal contacts and leads inserted into the hub.

Referring now to FIGS. 11-12, alternative embodiments of hubs 200 are depicted. In FIGS. 11-12, the hub 200 is generally octagonal. However, it will be understood that the hub may take any suitable shape. It may be desirable of the hub to have rounded corners, if any corners are present, for purposes of patient comfort or for reducing complications, such as skin erosion due to sharp corners or edges, when implanted. Alternatively or in addition, a polymeric coating, covering, boot, sheath, or the like may be placed about the hub to improve patient comfort or to prevent fluid ingress into the hub and its electrical connections. The hub 20 depicted in FIG. 11 is similar to the hubs depicted in FIGS. 3-9 in that different lead receptacles may have overlapping or common internal contacts 280. In the embodiment depicted in FIG. 12, each lead receptacle (indicated by dashed lines for two of the receptacles) has discrete contacts, with no overlapping or common contacts between receptacles (or in communication with different lead entry ports 210). Of course, in some embodiments, a hub may employ a combination of receptacles having common contacts and receptacles having no contacts in common with other receptacles.

In various embodiments, a hub as described herein is rotatable such that a single entry port can be used to deliver more than one lead to the hub. In one example, the top portion of the hub that contains the lead entry port would rotate relative to the base of the hub that contains the rows of electrical contacts that would be connected to the channels of the signal generator. This would result in one entry port that would still allow leads to be inserted into the hub and be aligned with multiple rows of contacts within the hub.

A hub, or components thereof, as described herein may be made of any suitable material and according to any suitable process. The hub may, in many respects, be manufactured in a manner similar to a lead extension or implantable signal generator. For example, the hub body form may be made from a metallic material, such as stainless steel or titanium, or polymeric material, such as polycarbonate, polysulfone, polyurethane, silicone or the like. The hub housing could be molded or otherwise formed into halves that could be welded or otherwise joined. Preferably, the hub housing is sealed in a manner sufficient to prevent bodily fluid from entering a seam.

It is also desired to prevent bodily fluid from entering a bore or from flowing through a bore to maintain electrical isolation of contacts in the bore of a hub. Wiper seals or other fluid seals that are well known in the art for use with lead extension or implantable electrical signal generators may be employed with the hubs described herein. For example, a wiper seal may be positioned in the bore at or near a port entrance of the hub or between contacts in a bore.

Lead receptacles, such as those known for implantable signal generators or lead extensions, with alternating insulating and conductive members may be fitted into bores of the hub. The cable extending from the hub for coupling the hub to an implantable electrical signal generator may include contacts for insertion into a lead receptacle of the signal generator, lead extension, adaptor, or the like. In many respects, techniques and materials employed for forming implantable medical leads may be used to form the cable.

Thus, embodiments of HUB FOR IMPLANTABLE MEDICAL LEADS are disclosed. One skilled in the art will appreciate that the present invention can be practiced with embodiments other than those disclosed. The disclosed embodiments are presented for purposes of illustration and not limitation, and the present invention is limited only by the claims that follow.

What is claimed is:

1. An implantable hub for electrically coupling one or more implantable leads to an active implantable electrical medical device capable of generating electrical signals on a plurality of discrete channels, the hub comprising:
   a first lead receptacle having a plurality of contacts for electrically coupling a lead to an implantable electrical device;
   a second lead receptacle having a plurality of contacts for electrically coupling a lead to the implantable electrical device;
   wherein at least one of the plurality of contacts of the first receptacle is a contact of the second receptacle;
   a cable configured to be inserted into the electrical device, the cable having contacts configured to electrically couple to internal contacts of the electrical device, wherein the contacts of the cable are electrically coupled to the contacts of the first and second receptacles; and
   a demultiplexer configured to create subchannels such that different contacts of the plurality of contacts of at least one of the first lead receptacle and second lead receptacle that correspond to a same channel of an active implantable electrical medical device can be activated at different times to effectively increase the number of channels of the plurality of discrete channels.

2. A hub according to claim 1, further comprising a third lead receptacle having a plurality of contacts for electrically coupling a lead to an implantable electrical device, wherein at least one of the plurality of contacts of the third lead receptacle is a contact of the second or first receptacle, and further wherein the demultiplexer is further configured to create subchannels such that different contacts of the plurality of contacts of at least one of the first, second, and third lead receptacles that correspond to a same channel of an active implantable electrical medical device can be activated at different times to effectively increase the number of channels of the plurality of discrete channels.

3. A hub according to claim 1, wherein the plurality of contacts of the first receptacle and the plurality of contacts of the second receptacle are disposed in a bore, wherein the first receptacle defines a first opening in communication with the bore and the second receptacle defines a second opening in communication with the bore.

4. A hub according to claim 3, wherein the bore is non-rectilinear.

5. A hub according to claim 3, further comprising a third lead receptacle having a plurality of contacts for electrically coupling a lead to an implantable electrical device, wherein at least one of the plurality of contacts of the third lead receptacle is a contact of the second or first receptacle, and wherein the third receptacle is disposed in the bore and defines an opening in communication with the bore.

6. A hub according to claim 1, wherein at least one contact of the cable is electrically coupled to more than one contact of the lead receptacles.

7. A system comprising:
   an implantable electrical medical device;
   a hub according to claim 1 electrically couplable to the implantable electrical medical device.

8. A system according to claim 7, further comprising a lead electrically couplable to the hub via insertion into a lead receptacle of the hub.

9. A hub according to claim 1, wherein at least one contact of the plurality of contacts of the first lead receptacle is a discrete contact.

10. A hub according to claim 9, wherein at least one contact of the plurality of contacts of the second lead receptacle is a discrete contact.

11. A hub according to claim 1, wherein the hub is configured to be implanted remotely from an active implantable electrical medical device and in proximity to a tissue site to which a lead is implanted.

12. An implantable hub for electrically coupling one or more implantable leads to an active implantable electrical medical device capable of generating electrical signals on a plurality of discrete channels, the hub comprising:
   a plurality of internal contacts for electrically coupling to one or more leads;
   a cable having a plurality of contacts for electrically coupling the hub to an electrical device; and
   a demultiplexer configured to create subchannels such that different contacts of the plurality of internal contacts that correspond to a same channel of an active implantable electrical medical device can be activated at different times to effectively increase the number of channels of the plurality of discrete channels;
   wherein each internal contact of the hub is electrically coupled to a single one of the plurality of contacts of the cable,
   wherein the number of internal contacts of the hub is greater than the number of contacts of the cable.

13. A hub according to claim 12, wherein the hub is configured to be implanted remotely from an implantable electrical medical device and in proximity to a tissue site to which one or more leads is implanted.

* * * * *